United States Patent
Trayanova et al.

(10) Patent No.: US 11,278,247 B2
(45) Date of Patent: Mar. 22, 2022

(54) RISK STRATIFICATION FOR VENTRICULAR ARRHYTHMIA IN PATIENTS WITH REPAIRED TETRALOGY OF FALLOT (TOF) VIA IMAGE-BASED COMPUTATIONAL SIMULATIONS

(71) Applicant: THE JOHNS HOPKINS UNIVERSITY, Baltimore, MD (US)

(72) Inventors: Natalia A. Trayanova, Baltimore, MD (US); Adityo Prakosa, Baltimore, MD (US); Mark Cartoski, Parkville, MD (US); Patrick M. Boyle, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 297 days.

(21) Appl. No.: 16/347,385

(22) PCT Filed: Nov. 6, 2017

(86) PCT No.: PCT/US2017/060119
§ 371 (c)(1),
(2) Date: May 3, 2019

(87) PCT Pub. No.: WO2018/085755
PCT Pub. Date: May 11, 2018

(65) Prior Publication Data
US 2020/0261028 A1   Aug. 20, 2020

Related U.S. Application Data

(60) Provisional application No. 62/417,903, filed on Nov. 4, 2016.

(51) Int. Cl.
*A61B 5/00* (2006.01)
*G16H 50/50* (2018.01)
(Continued)

(52) U.S. Cl.
CPC .......... *A61B 5/7275* (2013.01); *A61B 5/0044* (2013.01); *A61B 5/055* (2013.01);
(Continued)

(58) Field of Classification Search
CPC ........ G16H 50/50; G16H 50/30; G16H 30/40; G01R 33/5601; G01R 33/5608;
(Continued)

(56) References Cited

U.S. PATENT DOCUMENTS

| 2007/0014452 A1* | 1/2007 | Suresh ................. G06T 7/246 382/128 |
| 2014/0104644 A1 | 4/2014 | Hayakawa |

(Continued)

FOREIGN PATENT DOCUMENTS

| CA | 2827042 A1 | 8/2012 |
| WO | 2012109618 A2 | 8/2012 |

OTHER PUBLICATIONS

Folino et al. 2005 Indian Pacing and Electrophysiology J. 5:312-324 (Year: 2005).*
(Continued)

*Primary Examiner* — Keith M Raymond
*Assistant Examiner* — Patrick M Mehl
(74) *Attorney, Agent, or Firm* — MH2 Technology Law Group LLP

(57) ABSTRACT

An embodiment in accordance with the present invention provides a non-invasive solution to risk stratify the risk of in arrhythmia in patients with TOF. Currently, no reliable method for non-invasive risk stratification exists. In the realm of congenital heart disease, cardiac MRI is now used routinely for patients with Tetralogy of Fallot (TOF), the most common form of cyanotic congenital heart disease. An innovative platform for using clinical MRI data to create 3D electromechanical models of the heart enables predictions of (Continued)

whether or not patients with ischemic heart disease have the substrate for arrhythmia and what their relative risk for such an event is. An embodiment of the current invention provides a non-invasive solution to risk stratify the risk of arrhythmia in patients with TOF. Currently, no reliable method for non-invasive risk stratification exists.

18 Claims, 1 Drawing Sheet

(51) Int. Cl.
  *G16H 50/30* (2018.01)
  *G16H 30/40* (2018.01)
  *A61B 5/055* (2006.01)
  *G01R 33/56* (2006.01)

(52) U.S. Cl.
  CPC .......... *A61B 5/7207* (2013.01); *A61B 5/7264* (2013.01); *G01R 33/5601* (2013.01); *G01R 33/5608* (2013.01); *G16H 30/40* (2018.01); *G16H 50/30* (2018.01); *G16H 50/50* (2018.01); *A61B 2576/023* (2013.01)

(58) Field of Classification Search
  CPC ..... A61B 5/7275; A61B 5/0044; A61B 5/055; A61B 5/7207; A61B 5/7264; A61B 2576/023
  See application file for complete search history.

(56) References Cited

U.S. PATENT DOCUMENTS

| | | | | |
|---|---|---|---|---|
| 2014/0122048 | A1* | 5/2014 | Vadakkumpadan ... | G16H 50/30 703/11 |
| 2016/0082084 | A1* | 3/2016 | Janssens ................. | A61P 9/10 514/7.6 |

OTHER PUBLICATIONS

USCF 2011 Tetralogy of Fallot 4 pages; internet access https://surgery.ucsf.edu/conditions--procedures/tetralogy-of-fallot.aspx (Year: 2011).*

Vaujois et al. 2016 Diagnostic and Interventional Imaging 97:549-560; Pub.Date May 2016 (Year: 2016).*
American Heart Association 2002 Circulation 105:539-542; Pub. Date Jan. 29, 2002 (Year: 2002).*
Haddad et al. 2008 Circulation 117:1436-1448 (Year: 2008).*
Srivatsa 2014 e-Journal of the ESC Council for Cardiology Practice, 16 pages; Pub.Date Apr. 12, 2014; internet address https://www.escardio.org/Journals/E-Journal-of-Cardiology-Practice/Volume-12/A-proposed-technique-for-right-ventricular-septal-pacing (Year: 2014).*
Stephensen et al. 2014 Am. J. Physiol. Heart Circ. Physiol. 306:H895-H903 (Year: 2014).*
Yang et al. 2007 Computers and Structures 85:988-997 (Year: 2007).*
Molitoris et al. 2016 Integ. Biol. 8:230-242 (Year: 2016).*
Ben-Ari, M., et al., "Mathematical logic for computer science" Third Edition, Springer, 2012, p. 257.
Ctykajioba O.B. II ):Ip. MarHIITHo-pe30HaHCHM TOMorpaqnrn cep,n:u:a y 6oJThHhlX IImpapKTOM MIIOKap,n:a. Ky6aHCKIIii ttayqHhiii Me,n:IIU:IIHCKIIii BeCTHIIK, 2010, N2 6 (120), c. 134-139.
Dobson, R., et al., "Late gadolinium enhancement and adverse outcomes in a contemporary cohort of adult survivors of tetralogy of Fallot", Congenital Heart Disease 2017; vol. 12, pp. 58-66.
Dobson, et al., Late gadolinium enhancement and adverse outcomes in a contemporary cohort of adult survivors of tetralogy of Fallot. Congenit Heart Dis. Jan. 2017;12(1):58-66.
Babu-Narayan, et al., Ventricular fibrosis suggested by cardiovascular magnetic resonance in adults with repaired tetralogy of Fallot and its relationship to adverse markers of clinical outcome. Circulation. Jan. 24, 2006;113(3):405-13.
Arevalo, et al., Tachycardia in post-infarction hearts: insights from 3d image-based ventricular models. PLoS One. Jul. 2, 2013;8(7):e68872.
Chen, et al., Myocardial ECV fraction assessed by CMR is Associated with Type of Hemodynamic Load and Arrhythmia in Repaired Tetralogy of Fallot. JACC Cardiovasc Imaging. Jan. 2016;9(1):1-10.
Chiu, et al., Repolarization Altenans and Ventricular Arrhythmia in a Repaired Tetralogy of Fallot Animal Model. J Am Heart Assoc. Dec. 2015; 4(12): e002173.
Villafane, et al., Hot topics in tetralogy of Fallot. J Am Coll Cardiol. Dec. 10, 2013;62(23):2155-66.
Trayanova, et al., Advances in modeling ventricular arrhythmias: from mechanisms to the clinic. Wiley Interdiscip Rev Syst Biol Med. Mar.-Apr. 2014;6(2):209-24.

* cited by examiner

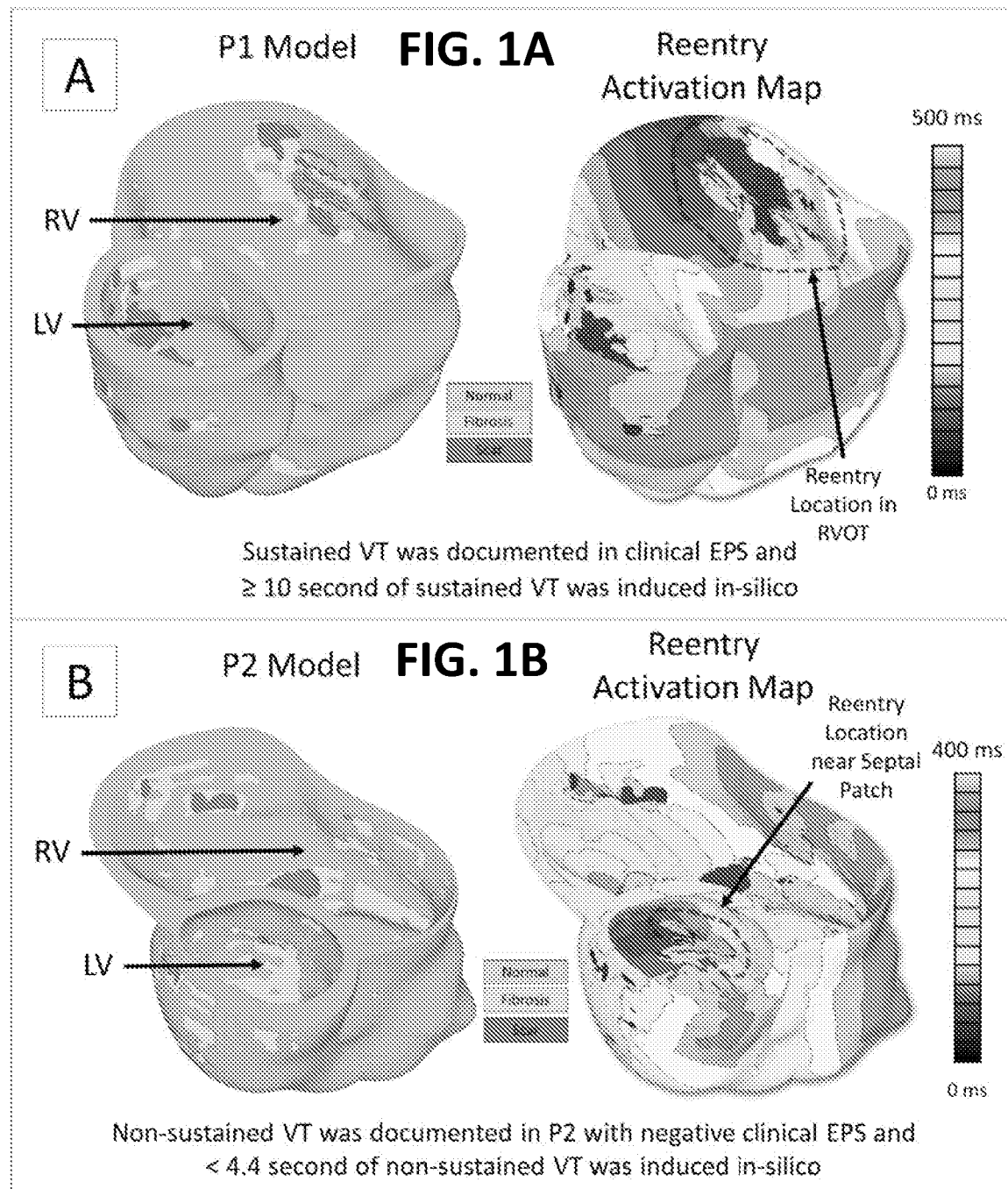

RISK STRATIFICATION FOR VENTRICULAR ARRHYTHMIA IN PATIENTS WITH REPAIRED TETRALOGY OF FALLOT (TOF) VIA IMAGE-BASED COMPUTATIONAL SIMULATIONS

CROSS-REFERENCE TO RELATED APPLICATIONS

This application is a 35 U.S.C. § 371 U.S. national entry of International Application PCT/US2017/060119, having an international filing date of Nov. 6, 2017, which claims the benefit of U.S. Provisional Application No. 62/417,903, filed Nov. 4, 2016, the content of each of the aforementioned applications is herein incorporated by reference in their entirety.

GOVERNMENT RIGHTS

This invention was made with government support under grant numbers 1DP1HL123271-01 and T32HL125239, awarded by the National Institutes of Health. The government has certain rights in the invention.

FIELD OF THE INVENTION

The field of the currently claimed embodiments of this invention relates to computer-generated risk stratification for ventricular arrhythmia in patients with repaired Tetralogy of Fallot, and more particularly to computer model-based risk stratification for ventricular arrhythmia in patients with repaired Tetralogy of Fallot using image-based computer simulations.

BACKGROUND OF THE INVENTION

Patients with repaired Tetralogy of Fallot (TOF) have increased arrhythmia risk due to myocardial fibrosis, scar and right ventricular dilation. Current risk stratification lacks consistent predictive value and clinical practicality. TOF hearts are quite unique in terms of their geometry, scar profile, and etiology of arrhythmia. In the TOF cohort, 43% of patients have a sustained arrhythmia or an intervention for an arrhythmia in their lifetime. Roughly 10% of patients with TOF develop high grade ventricular arrhythmia. This degree of pathologic rhythm disturbances is due to scar formation and fibrosis from surgery and years of pulmonary valve disease. The current clinical practice is to use various methods of risk stratification in an attempt to get a rough composite of what a patient's arrhythmia potential is. These methods are based on surface ECG findings, Holter monitor recordings, clinical events such as syncope, and MRI metrics such as right ventricular volume. All of these measures have yet to provide a reliable method for risk stratification.

Therefore, it would be advantageous to provide improved methods and systems for risk stratification for ventricular arrhythmia in patients with repaired TOF.

SUMMARY OF THE INVENTION

The foregoing needs are met, to a great extent, by the present invention, wherein in one aspect a method of providing computer-generated risk stratification for ventricular arrhythmia in a patient with Tetralogy of Fallot includes receiving contrast-agent-enhanced magnetic resonance imaging (MRI) data of the patient's heart. The patient's heart was previously repaired for correction of at least one congenital heart defect comprising Tetralogy of Fallot. The method includes constructing a three-dimensional computer model of at least right and left ventricles of said patient's heart using said contrast-agent-enhanced MRI data and pre-defined rules to set mechanical and electrical properties of local tissue regions within said right and left ventricles, said right ventricle having an abnormal geometry. The method includes performing at least one simulation of electromechanical function of said patient's heart using said three-dimensional computer model. The method includes testing simulated electromechanical function of said patient's heart, a plurality of times, during said at least one simulation, by applying a corresponding plurality of electrical stimulations at a respective plurality of stimulation points of said right and left ventricles to provide a plurality of electromechanical function outcomes. The method also includes classifying each of said plurality of electromechanical function outcomes as at least one of exhibiting normal electromechanical function or exhibiting ventricular arrhythmic electromechanical function. The method includes providing a risk stratification for ventricular arrhythmia in said patient based on said classified plurality of simulations, wherein said pre-defined rules comprise assigning a tissue type to said local tissues regions within said right and left ventricles. Further, the method includes displaying a visual representation of the three-dimensional computer model of the patient's heart wherein the visual representation comprises a visual representation of the electromagnetic activity of the patient's heart.

In accordance with an aspect of the present invention, the tissue type includes at least normal tissue, fibrotic tissue, scar tissue, and surgical patch material. Pre-defined rules further include setting said mechanical and electrical properties of local tissue regions based at least partially on a location of each of said local tissue region within said patient's heart. Pre-defined rules further include setting said mechanical and electrical properties of fibrotic tissue regions using said contrast-agent-enhanced MRI data. Pre-defined rules further include setting said mechanical and electrical properties of fibrotic tissue regions each to one of a plurality of values corresponding to an intensity histogram of said contrast-agent-enhanced MRI data. Electrical properties include direction-dependent electrical conductivity corresponding to direction-dependent electrical properties of corresponding heart tissue resulting from tissue fiber orientations. The location of each of said local tissue regions within said patient's heart is determined based on standard heart subsections. The plurality of stimulation points of said right and left ventricles are selected to probe at least each anatomical subsection in each of said right and left ventricles of said three-dimensional computer model. Each said anatomical subsection is one of a basal, medial, apical, lateral, septal, posterior, or anterior anatomical subsection. The plurality of stimulation points of said right and left ventricles are at least 9 stimulation points in said right ventricle and at least 17 stimulation points in said left ventricle. The plurality of stimulation points of said right and left ventricles are automatically placed by a computer using predetermined rules. Constructing a three-dimensional computer model of at least right and left ventricles of said patient's heart using said contrast-agent-enhanced MRI data and pre-defined rules includes segmenting geometry of said at least right and left ventricles of said patient's heart using at least three different perspective views within stacks of contrast-agent-enhanced MRI images and taking into account motion of a myocardial wall within CINE images to help discern myocardial boundaries. Constructing a three-dimensional computer model of at least right and left ventricles of said patient's heart using said contrast-agent enhanced MRI data and pre-defined rules includes segmenting abnormal geometry of at least right and left ventricles of said patient's heart using at least three different perspective planes with simultaneous comparisons to CINE MRI images of said patient's heart to define abnormal geometry of said right ventricle. A computer-readable medium including non-transient computer-executable code can be used to perform the method. A computer processor can also be used to perform the methods.

In accordance with an aspect of the present invention, a system for providing computer-generated risk stratification for ventricular arrhythmia in a patient with Tetralogy of Fallot includes an imaging modality configured for generating contrast-agent enhanced magnetic resonance image data of the patient's heart. The system also includes anon-transitory computer readable medium configured for receiving contrast-agent-enhanced magnetic resonance imaging (MRI) data of the patient's heart, wherein the patient's heart includes at least one congenital heart defect comprising Tetralogy of Fallot. The non-transitory computer readable medium is programmed for constructing a three-dimensional computer model of at least right and left ventricles of said patient's heart using said contrast-agent-enhanced MRI data and pre-defined rules to set mechanical and electrical properties of local tissue regions within said right and left ventricles, said right ventricle having an abnormal geometry. The non-transitory computer readable medium is programmed for performing at least one simulation of electromechanical function of said patient's heart using said three-dimensional computer model. The non-transitory computer readable medium is programmed for testing simulated electromechanical function of said patient's heart, a plurality of times, during said at least one simulation, by applying a corresponding plurality of electrical stimulations to provide a plurality of electromechanical function outcomes. The non-transitory computer readable medium is programmed for classifying each of said plurality of electromechanical function outcomes as at least one of exhibiting normal electromechanical function or exhibiting ventricular arrhythmic electromechanical function. The non-transitory computer readable medium is also programmed for providing a risk stratification for ventricular arrhythmia in said patient based on said classified plurality of simulations, wherein said pre-defined rules comprise assigning a tissue type to said local tissues regions within said right and left ventricles. Further, the non-transitory computer readable medium is programmed for displaying a visual representation of the three-dimensional computer model of the patient's heart wherein the visual representation comprises a visual representation of the electromagnetic activity of the patient's heart.

In accordance with yet another aspect of the present invention, the tissue type includes at least normal tissue, fibrotic tissue, scar tissue, and surgical patch material. Pre-defined rules further include setting said mechanical and electrical properties of local tissue regions based at least partially on a location of each of said local tissue region within said patient's heart. Pre-defined rules further include setting said mechanical and electrical properties of fibrotic tissue regions using said contrast-agent-enhanced MRI data. Pre-defined rules further include setting said mechanical and electrical properties of fibrotic tissue regions each to one of a plurality of values corresponding to an intensity histogram of said contrast-agent-enhanced MRI data.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 1A and 1B also illustrate an exemplary visual output, according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a non-invasive solution to risk stratify the risk of arrhythmia in patients with TOF. Currently, no reliable method for non-invasive risk stratification exists. In the realm of congenital heart disease, cardiac MRI is now used routinely for patients with Tetralogy of Fallot (TOF), the most common form of cyanotic congenital heart disease. An innovative platform for using clinical MRI data to create 3D electromechanical models of the heart enables predictions of whether or not patients with ischemic heart disease have the substrate for arrhythmia and what their relative risk for such an event is. An embodiment of the current invention provides a non-invasive solution to risk stratify the risk of arrhythmia in patients with TOF. Currently, no reliable method for non-invasive risk stratification exists.

A non-invasive method to identify the optimal ablation sites for infarct-related ventricular tachycardia (VT) by using 3D electrophysiological heart simulations with a model reconstructed from the patient's late gadolinium-enhanced (LGE) MRI image is disclosed in PCT/US2012/024759, filed Feb. 10, 2012, the entire contents of which is incorporated herein by reference. In this application, that methodology is extended to patients with Tetralogy of Fallot (TOF), the most common form of cyanotic congenital heart disease.

Personalized models developed from cardiac late gadolinium enhancement MRI (LGE-MRI) could correctly assess risk of arrhythmia in patients with repaired TOF using a Virtual Arrhythmia Risk Prediction (VARP) protocol. The "virtual heart" methodology based on patient-specific model construction from MRI data has been leveraged herein to be able to stratify which patients have risk of arrhythmia and may need an ablation, implanted device, or earlier surgical intervention. The ability to predict arrhythmia risk, in the non-invasive way as in some embodiments of the current invention, would be extremely valuable and change the clinical approach to managing patients with repaired TOF.

There are numerous difficulties encountered with respect to TOF hearts that required solutions. For example, TOF assessment is typically performed on newborn or very young babies. Consequently, heart image data not only has the problem that the patient's heart is beating and requires images to be taken in relatively short periods that rule out currently available diffusion tensor MRI, but the subject hearts are much smaller than adult hearts. In addition, TOF patients typically have abnormally shaped hearts, especially the right ventricle. Furthermore, TOF hearts, after surgical repair, have patches closing the abnormal opening between ventricles resulting from the birth defect. The patches themselves, as well as potentially scar tissue around the patches, have important effects on the functioning of the heart. Some of these features are described in more detail, as follows.

In Tetralogy of Fallot (ToF), a congenital heart disease, the shape of the heart is different. The right ventricle is very dilated (ballooned). The reconstruction of the geometry of the ToF heart, thus provides some unique challenges. In some applications, segmentation is done for each of the 2D short axis slices, and then the 2D segmentations are used to reconstruct the full 3D ventricular geometry. In contrast, according to some embodiments of the current invention, segmentation and reconstruction is done in 3D by observing the delineation (segmentation) in 3 views: 4 chamber, 2 chamber, and a short axis view. In addition, CINE images are used to help discern myocardial boundaries. This allows the capture of the irregularity in the ventricular geometry of surgically-repaired ToF patients.

For model construction, according to some embodiments of the present invention, LGE-MRI scans (scans with a contrast agent) are used, so that structural changes (such as scar) in the tissue can be reconstructed. However, in ToF there are not "different tissue types including a normal tissue region, a scar tissue region and a transition zone region", but rather normal tissue region, fibrosis (distributed everywhere, in both left and right ventricles), and a surgical repair region (a synthetic patch that closes the ventricular septal defect).

The image reconstruction of "fibrosis and surgical repair regions" within the ventricular walls in ToF is different from "scar tissue region and a transition zone region" reconstruction. According to some embodiments of the present invention, histograms of signal intensity distribution and their standard deviations are used rather than a threshold cutoff to outline the different regions.

In previous modeling work, directed to hearts without ToF, the infarct was in the left ventricle, so the right ventricles consisted of normal tissue. Here, in the hearts with ToF, the right ventricle has fibrosis. That means that the right ventricle, for previous models, was more of a "passive conduit" for propagation of electrical waves during arrhythmia, but here it is no longer a bystander—it can generate arrhythmias. This generation of arrhythmias by the right ventricle necessitates that the right ventricle and the fibrosis it contains be carefully reconstructed.

Stimuli is given to elicit potential arrhythmias from many more locations in the ventricles than in previous applications and modeling methods. In the present invention, the stimulation points are uniformly distributed throughout all segments and regions of both the left and the right ventricles, so that the arrhythmia-inducing potential of both the left and the right ventricles, which have distributed fibrosis and a septal repair patch, can be captured in the model. In previous modeling, stimulation was applied mostly from points in the left ventricle, and only at 2 locations in the right ventricle, because the right ventricle was not an arrhythmogenic zone. Also, the number of stimulation points in the present invention is much larger overall, because activity associated with the distributed fibrosis must be captured, rather than the more compact infarct in the left ventricle as in previous modelling modalities. Also the stimulation points in the model of the present invention can be placed using automated software, without manual intervention, according to an embodiment of the current invention.

Some embodiments of the current invention can provide software capable of modeling fibrosis within the right ventricle; and/or software capable of using MRI data to assign risk of arrhythmia in patients with repaired TOF. The following examples help explain and illustrate concepts of the current invention. The broad concepts of this invention are not limited to the particular examples, and the examples contained herein are not intended to be limiting.

In one example, risk stratification for ventricular arrhythmia in patients with repaired TOF is modelled via image-based computational simulations. In this exemplary implementation of the present invention, patients with repaired TOF have increased arrhythmia risk due to myocardial fibrosis, scar and right ventricular dilation. Current risk stratification lacks consistent predictive value and clinical practicality. Therefore, this example shows that personalized models developed from cardiac late gadolinium enhancement MRI (LGE-MRI) could correctly assess risk of arrhythmia in patients with repaired TOF using a Virtual Arrhythmia Risk Prediction (VARP) protocol.

As a proof-of-concept retrospective study, personalized 3D computational models of TOF hearts from LGE-MRI scans were developed. Three patients with clinically disparate arrhythmia status were included: patient 1 (P1) had clinical episodes of sustained ventricular tachycardia (VT) and inducibility in electrophysiologic study (EPS); patient 2 (P2) had negative EPS despite documented runs of non-sustained VT; patient 3 (P3) had no clinical evidence of VT. Then, for each heart, the VARP protocol was applied to generate a computational model, including personalized representations of scar and fibrosis. The inducibility of reentrant arrhythmia from 26 pacing sites was then assessed.

For all three cases, VARP outcomes correlated with clinical observations. In the P1 model sustained VT was induced with rapid ventricular pacing, while only non-sustained VT was induced in the P2 model, as illustrated in FIGS. 1A and 1B. No arrhythmia was induced in the P3 model. Reentrant wavefronts in P1 and P2 occurred near the right ventricular outflow tract (RVOT) or ventricular septal defect patch, common sites of reentry observed in EPS in patients with TOF, as illustrated in FIGS. 1A and 1B. FIG. 1A illustrates a heart model and reentry map according to an embodiment of the present invention, where sustained VT was documented in clinical EPS and ≥10 seconds of sustained VT was induced in-silico. FIG. 1B illustrates a heart model and reentry map according to an embodiment of the present invention, where non-sustained VT was documented in P2 with negative clinical EPS and <4.4 seconds of non-sustained VT was induced in-silico.

FIGS. 1A and 1B also illustrate an exemplary visual output, according to an embodiment of the present invention. The display transforms image data from the heart of the subject into a model and a reentry map that shows types of tissue within the heart and also location of reentry for the heart of the subject.

Application of the VARP approach in repaired TOF patients is feasible and has the potential to correctly identify patients with a high risk of developing arrhythmia. With additional validation this non-invasive technique could serve as an effective tool or longitudinal risk assessment and help guide clinical decision making.

Display of visual images or data related to the device and procedure of the present invention can be carried out using a computer, non-transitory computer readable medium, or alternately a computing device or non-transitory computer readable medium incorporated into the computing device or the imaging device.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer. The operating console is a non-generic computer specifically designed by the manufacturer. It is not a standard business or personal computer that can be purchased at a local store. Additionally, the console computer can carry out communications with the scanner through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of providing computer-generated risk stratification for ventricular arrhythmia in a patient with Tetralogy of Fallot, comprising:
    receiving contrast-agent-enhanced magnetic resonance imaging (MRI) data of the patient's heart, said patient's heart having been previously repaired for correction of at least one congenital heart defect comprising Tetralogy of Fallot;
    constructing a three-dimensional computer model of at least right and left ventricles of said patient's heart using said contrast-agent-enhanced MRI data and pre-defined rules to set mechanical and electrical properties of local normal tissue, fibrotic tissue, scar tissue, and surgical patch material regions within said right and left ventricles, said right ventricle having an abnormal geometry, wherein said constructing comprises segmenting at least a right ventricle of said patient's heart using at least a four chamber view, a two chamber view, and a short axis view;
    performing at least one simulation of electromechanical function of said patient's heart using said three-dimensional computer model;
    testing simulated electromechanical function of said patient's heart, a plurality of times, during said at least one simulation, by applying a corresponding plurality of electrical stimulations at a respective plurality of stimulation points of said right and left ventricles to provide a plurality of electromechanical function outcomes;
    classifying each of said plurality of electromechanical function outcomes as at least one of exhibiting normal electromechanical function or exhibiting ventricular arrhythmic electromechanical function;
    providing a risk stratification for ventricular arrhythmia in said patient based on said classified plurality of simulations, wherein said pre-defined rules comprise assigning a tissue type to said local tissues regions within said right and left ventricles; and
    displaying a visual representation of the three-dimensional computer model of the patient's heart wherein the visual representation comprises the electromagnetic activity of the patient's heart.

2. The method of claim 1, wherein said pre-defined rules further comprise setting said mechanical and electrical properties of local tissue regions based at least partially on a location of each of said local tissue region within said patient's heart.

3. The method of claim 1, wherein said pre-defined rules further comprise setting said mechanical and electrical properties of fibrotic tissue regions using said contrast-agent-enhanced MRI data.

4. The method of claim 2, wherein said pre-defined rules further comprise setting said mechanical and electrical properties of fibrotic tissue regions each to one of a plurality of values corresponding to an intensity histogram of said contrast-agent-enhanced MRI data.

5. The method of claim 1, wherein said electrical properties include direction-dependent electrical conductivity corresponding to direction-dependent electrical properties of corresponding heart tissue resulting from tissue fiber orientations.

6. The method of claim 1, wherein said location of each of said local tissue region within said patient's heart is determined based on standard heart subsections.

7. The method of claim 1, wherein said plurality of stimulation points of said right and left ventricles are selected to probe at least each anatomical subsection in each of said right and left ventricles of said three-dimensional computer model.

8. The method of claim 7, wherein each said anatomical subsection is one of a basal, medial, apical, lateral, septal, posterior, or anterior anatomical subsection.

9. The method of claim 1, wherein said plurality of stimulation points of said right and left ventricles are at least 9 stimulation points in said right ventricle and at least 17 stimulation points in said left ventricle.

10. The method of claim 9, wherein said plurality of stimulation points of said right and left ventricles are automatically placed by a computer using the pre-defined rules.

11. The method of claim 1, wherein said constructing a three-dimensional computer model of at least right and left ventricles of said patient's heart using said contrast-agent-enhanced MRI data and pre-defined rules includes segmenting geometry of said at least right and left ventricles of said patient's heart taking into account motion of a myocardial wall within CINE images to help discern myocardial boundaries.

12. The method of claim 1, wherein said constructing a three-dimensional computer model of at least right and left ventricles of said patient's heart using said contrast-agent enhanced MRI data and pre-defined rules includes segmenting abnormal geometry of at least right and left ventricles of said patient's heart using comparisons to CINE MRI images of said patient's heart to define abnormal geometry of said right ventricle.

13. A non-transitory computer-readable medium comprising computer-executable code, which when executed by a computer, causes the computer to perform actions comprising:
   receiving contrast-agent-enhanced magnetic resonance imaging (MRI) data of a patient's heart, said patient's heart having been previously repaired for correction of at least one congenital heart defect comprising Tetralogy of Fallot;
   constructing a three-dimensional computer model of at least right and left ventricles of said patient's heart using said contrast-agent-enhanced MRI data and pre-defined rules to set mechanical and electrical properties of local normal tissue, fibrotic tissue, scar tissue, and surgical patch material regions within said right and left ventricles, said right ventricle having an abnormal geometry, wherein said constructing comprises segmenting at least a right ventricle of said patient's heart using at least a four chamber view, a two chamber view, and a short axis view;
   performing at least one simulation of electromechanical function of said patient's heart using said three-dimensional computer model;
   testing simulated electromechanical function of said patient's heart, a plurality of times, during said at least one simulation, by applying a corresponding plurality of electrical stimulations at a respective plurality of stimulation points of said right and left ventricles to provide a plurality of electromechanical function outcomes;
   classifying each of said plurality of electromechanical function outcomes as at least one of exhibiting normal electromechanical function or exhibiting ventricular arrhythmic electromechanical function;
   providing a risk stratification for ventricular arrhythmia in said patient based on said classified plurality of simulations, wherein said pre-defined rules comprise assigning a tissue type to said local tissues regions within said right and left ventricles; and
   displaying a visual representation of the three-dimensional computer model of the patient's heart wherein the visual representation comprises the electromagnetic activity of the patient's heart.

14. A system comprising a computer processor configured to perform actions comprising:
   receiving contrast-agent-enhanced magnetic resonance imaging (MRI) data of a patient's heart, said patient's heart having been previously repaired for correction of at least one congenital heart defect comprising Tetralogy of Fallot;
   constructing a three-dimensional computer model of at least right and left ventricles of said patient's heart using said contrast-agent-enhanced MRI data and pre-defined rules to set mechanical and electrical properties of local normal tissue, fibrotic tissue, scar tissue, and surgical patch material regions within said right and left ventricles, said right ventricle having an abnormal geometry, wherein said constructing comprises segmenting at least a right ventricle of said patient's heart using at least a four chamber view, a two chamber view, and a short axis view;
   performing at least one simulation of electromechanical function of said patient's heart using said three-dimensional computer model;
   testing simulated electromechanical function of said patient's heart, a plurality of times, during said at least one simulation, by applying a corresponding plurality of electrical stimulations at a respective plurality of stimulation points of said right and left ventricles to provide a plurality of electromechanical function outcomes;
   classifying each of said plurality of electromechanical function outcomes as at least one of exhibiting normal electromechanical function or exhibiting ventricular arrhythmic electromechanical function;
   providing a risk stratification for ventricular arrhythmia in said patient based on said classified plurality of simulations, wherein said pre-defined rules comprise assigning a tissue type to said local tissues regions within said right and left ventricles; and
   displaying a visual representation of the three-dimensional computer model of the patient's heart wherein the visual representation comprises the electromagnetic activity of the patient's heart.

15. A system for providing computer-generated risk stratification for ventricular arrhythmia in a patient with Tetralogy of Fallot comprising:
   an imaging modality configured for generating contrast-agent enhanced magnetic resonance image data of the patient's heart;
   a non-transitory computer readable medium configured for:
   receiving contrast-agent-enhanced magnetic resonance imaging (MRI) data of the patient's heart, wherein the patient's heart includes at least one congenital heart defect comprising Tetralogy of Fallot;
   constructing a three-dimensional computer model of at least right and left ventricles of said patient's heart using said contrast-agent-enhanced MRI data and pre-defined rules to set mechanical and electrical properties of local normal tissue, fibrotic tissue, scar tissue, and surgical patch material regions within said right and left ventricles, said right ventricle having an abnormal geometry, wherein said constructing comprises segmenting at least a right ventricle of said patient's heart using at least a four chamber view, a two chamber view, and a short axis view;
   performing at least one simulation of electromechanical function of said patient's heart using said three-dimensional computer model;
   testing simulated electromechanical function of said patient's heart, a plurality of times, during said at least one simulation, by applying a corresponding plurality of electrical stimulations to provide a plurality of electromechanical function outcomes;
   classifying each of said plurality of electromechanical function outcomes as at least one of exhibiting normal electromechanical function or exhibiting ventricular arrhythmic electromechanical function;
   providing a risk stratification for ventricular arrhythmia in said patient based on said classified plurality of simulations, wherein said pre-defined rules comprise assigning a tissue type to said local tissues regions within said right and left ventricles; and displaying a visual representation of the three-dimensional computer model of the patient's heart wherein the visual representation comprises the electromagnetic activity of the patient's heart.

16. The system of claim 15, wherein said pre-defined rules further comprise setting said mechanical and electrical properties of local tissue regions based at least partially on a location of each of said local tissue region within said patient's heart.

17. The system of claim 15, wherein said pre-defined rules further comprise setting said mechanical and electrical properties of fibrotic tissue regions using said contrast-agent-enhanced MRI data.

18. The system of claim 16, wherein said pre-defined rules further comprise setting said mechanical and electrical properties of fibrotic tissue regions each to one of a plurality of values corresponding to an intensity histogram of said contrast-agent-enhanced MRI data.

* * * * *